(12) United States Patent
Viachaslau et al.

(10) Patent No.: US 8,707,763 B2
(45) Date of Patent: Apr. 29, 2014

(54) METHOD FOR THE ACCURATE MEASUREMENT OF THE DENSITY OF A SAMPLE

(75) Inventors: Urvantsau Viachaslau, Fontenay le Marmion (FR); Borys Richard, Caen (FR)

(73) Assignee: Instrumentation Scientifique de Laboratoire, Verson (FR)

( * ) Notice: Subject to any disclaimer, the term of this patent is extended or adjusted under 35 U.S.C. 154(b) by 246 days.

(21) Appl. No.: 13/173,182

(22) Filed: Jun. 30, 2011

(65) Prior Publication Data
US 2012/0073368 A1 Mar. 29, 2012

(30) Foreign Application Priority Data
Jul. 2, 2010 (FR) ...................................... 10 55354

(51) Int. Cl.
*G01N 9/00* (2006.01)
(52) U.S. Cl.
USPC ......................................................... 73/32 A
(58) Field of Classification Search
USPC ......................................................... 73/32 A
See application file for complete search history.

(56) References Cited

U.S. PATENT DOCUMENTS

| 4,491,009 | A | * | 1/1985 | Ruesch | 73/32 A |
| 4,655,075 | A | * | 4/1987 | Albert et al. | 73/32 A |
| 5,883,478 | A | * | 3/1999 | Thesling | 318/119 |
| 2008/0115577 | A1 | * | 5/2008 | Headrick | 73/32 A |

* cited by examiner

*Primary Examiner* — Hezron E Williams
*Assistant Examiner* — Mark A Shabman
(74) *Attorney, Agent, or Firm* — Faegre Baker Daniels LLP

(57) ABSTRACT

A method for the accurate measurement of the density of a sample using a densimeter equipped with a measurement cell, a sample-containing U-tube including a ferromagnetic member, an insulated conductive reading plate maintained at a different potential relative to the U-tube, and an electromagnetic excitation winding. The method includes the steps of transmitting a synchronised rectangular excitation signal continuously to the U-tube to cause the U-tube to vibrate at resonance frequency, the vibration being represented by a sinusoidal resonance signal; determining the resonance frequency from the variations in the voltage at the terminals of the capacitor and deducing an approximate value of the density of the sample; controlling the pulse width of the rectangular excitation signal to maintain a predefined constant amplitude of the resonance signal; and deducing a correction factor dependent on the viscosity of the sample.

1 Claim, 4 Drawing Sheets

METHOD FOR THE ACCURATE MEASUREMENT OF THE DENSITY OF A SAMPLE

CROSS-REFERENCE TO RELATED APPLICATION

This application claims priority to French Patent Application No. 10 55 354 filed Jul. 2, 2010, the disclosure of which is hereby explicitly incorporated by reference herein.

BACKGROUND OF THE INVENTION

1. Field of the Invention.

The present invention relates to a method for the accurate measurement of the density of a sample.

2. Description of the Related Art.

Of the physical measurements which have to be effected in the context of industrial processes, that of density figures among the most frequently necessary.

To that end, manufacturers market a range of densimeters based on various principles, all of which have advantages and disadvantages.

A densimeter which can be used in a satisfactory manner to measure the density of a sample is equipped with a measurement cell comprising the following elements:

a substantial enclosure which has very good heat conductivity and which defines at its inner portion a measurement chamber closed by a stopper;

a U-tube which is kept earthed and is secured to the stopper and which is to be filled with the sample being analyzed and extends inside the measurement chamber;

an insulated conductive reading plate maintained at a difference in potential relative to the U-tube and secured to the stopper in a position facing that tube in order to define a capacitor therewith;

an electromagnetic excitation winding mounted in a housing of the enclosure at right-angles to the ferromagnetic member; and means for operating the winding as well as means for reading the voltage at the terminals of the capacitor.

The U-tube of the cell of a densimeter of that type comprises, on the one hand, a central limb equipped with a ferromagnetic member at its middle portion and, on the other hand, two lateral limbs projecting outwardly from the measurement chamber to permit the injection of the sample being analyzed into the U-tube and the evacuation of that sample.

The principle of measuring the density of a sample by means of such a densimeter consists in causing the U-tube to vibrate at resonance frequency and in determining that frequency from the variations in the voltage at the terminals of the capacitor.

The resonance frequency enables the density of the sample being analyzed to be calculated to a first approximation on the basis of a standard equation known per se and from a preliminary calibration of the densimeter.

Such a calculation is, however, admissible only if an accuracy greater than $e^{-4}$ g/ml is not required because it does not take into account the damping effect caused by the viscosity of the sample.

Various algorithms have already been proposed to take that viscosity parameter into account but they all have the disadvantage of requiring several measurements, which makes them both time-consuming and onerous.

SUMMARY OF THE INVENTION

The present invention provides a method for the accurate measurement of the density of a sample by means of a densimeter cell.

According to the invention, the first step of this method includes injecting the sample being analyzed into the U-tube of the cell.

The following step includes operating the means for driving the winding in order to transmit continuously to the U-tube a synchronised rectangular excitation signal causing the tube to vibrate at resonance frequency.

The vibration brings about constant variations in the voltage at the terminals of the capacitor which are represented on an oscillograph by a sinusoidal resonance signal $V=f(t)$.

The excitation signal is centred relative to the zero of the resonance signal.

More specifically, it is known that the density d of a fluid is approximately a linear function of the square of the resonance period $T_R$ which can be determined from the resonance signal and therefore from the variations in the voltage at the terminals of the capacitor.

For a given densimeter, this straight line $d=f(T_R)^2$ can be created in a preliminary calibration step of obtaining two reference points from products whose density is known.

The calibration is effected as a general rule by injecting pure water and dry air into the U-tube.

An approximate value of the density of a sample being analyzed can then be read on the straight line $d=f(T_R)^2$ created in the preliminary calibration step.

That approximate density value is, however, erroneous in as much as it does not take the viscosity of the sample into account.

In order for the sinusoidal resonance signal representing the vibration of the U-tube to be as "clean" as possible, and for its amplitude not to decrease over time, the rectangular excitation signal, which transmits the energy to be supplied in order to maintain that amplitude, must have a width which is greater, the more viscous the sample being analyzed.

In order to take that requirement into account, it is proposed according to the invention to monitor and control the pulse width of the rectangular excitation signal in such a manner as to maintain the amplitude of the resonance signal at a predefined constant value.

The pulse width so regulated makes it possible to determine, in another step of the method according to the invention, a correction factor which depends on the viscosity of the sample being analyzed.

The actual density of the sample can then be calculated on the basis of the approximate value of the previously determined density and on the basis of the correction factor.

The method according to the invention thus has the advantage that it facilitates obtaining simultaneously an approximate value of the density of a sample being analyzed and a correction factor dependent on the viscosity of that sample, which value and factor enable the actual density of the sample to be calculated accurately in a later step.

In one form thereof, the present invention provides a method for the accurate measurement of the density of a sample by means of a densimeter equipped with a measurement cell comprising:

a substantial enclosure which has very good heat conductivity and which defines at its inner portion a measurement chamber closed by a stopper;

a U-tube which is kept earthed and is to be filled with the sample being analyzed and which extends inside the measurement chamber, the U-tube comprising a central limb equipped with a ferromagnetic member at its middle portion, as well as two lateral limbs secured to the stopper at their free ends and projecting outwardly from the measurement chamber to permit the injection of the sample being analyzed into the U-tube and the evacuation of that sample;

an insulated conductive reading plate maintained at a difference in potential relative to the U-tube and secured to the stopper in a position facing the tube in order to define a capacitor therewith;

an electromagnetic excitation winding mounted in a housing of the enclosure at right-angles to the ferromagnetic member; and means for driving the winding as well as means for reading the capacity of the capacitor, which method is characterized by the following steps:

the sample being analyzed is injected into the U-tube;

the means for driving the winding are operated in such a manner that it transmits continuously to the U-tube a synchronised rectangular excitation signal causing the tube to vibrate at resonance frequency, the vibration being represented by a sinusoidal resonance signal;

the resonance frequency is determined from the variations in the voltage at the terminals of the capacitor and an approximate value of the density of the sample being analyzed is deduced therefrom on the basis of a standard equation known per se;

the pulse width of the rectangular excitation signal is controlled in order to maintain a predefined constant amplitude of the resonance signal and a correction factor dependent on the viscosity of the sample being analyzed is deduced therefrom; and the actual density of the sample being analyzed is calculated on the basis of the approximate value of the previously determined density and on the basis of the correction factor.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
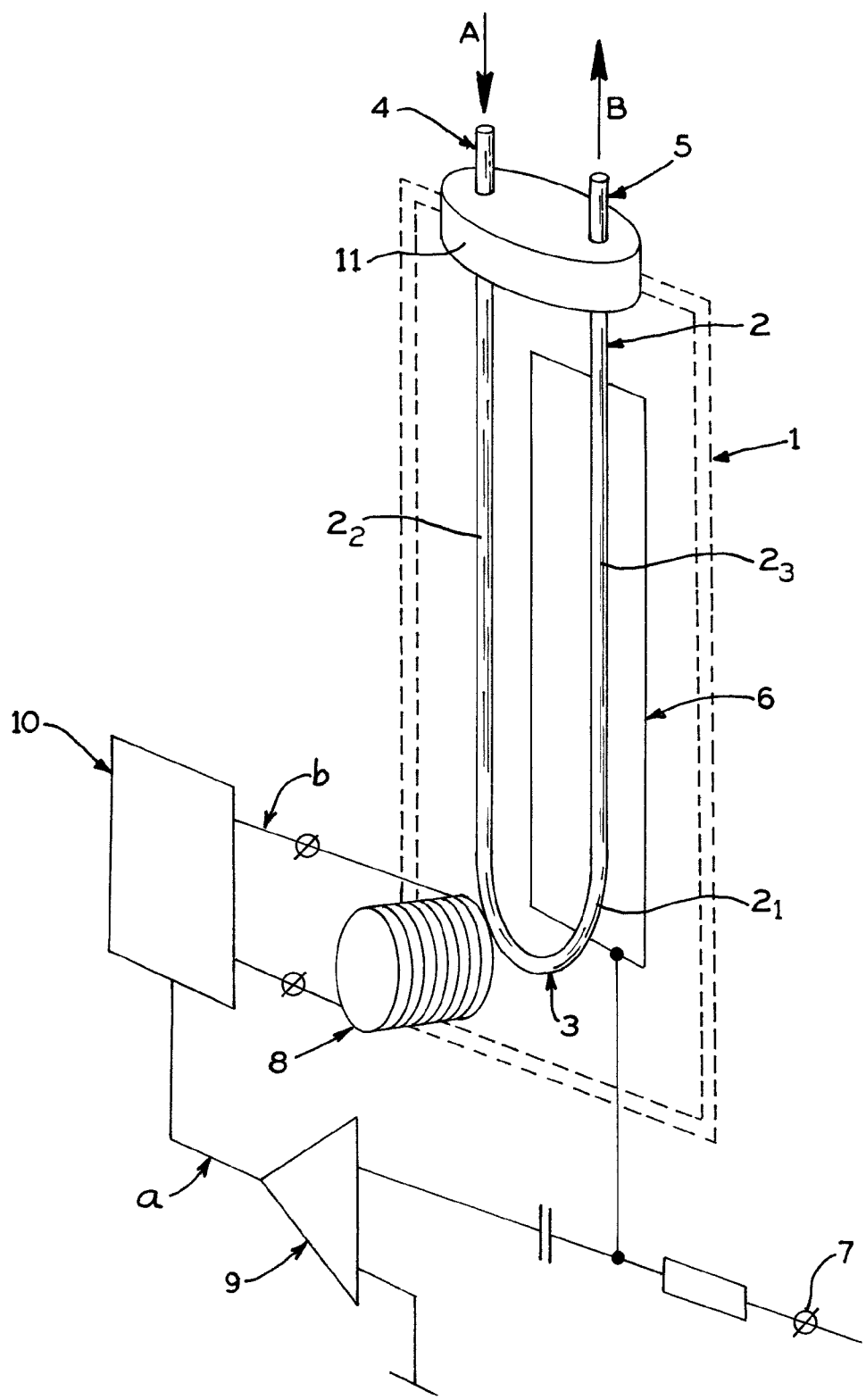
FIG. 1 is a diagram illustrating the configuration of the measurement cell of the densimeter used in accordance with the invention.

Corresponding reference characters indicate corresponding parts throughout the several views. Although the exemplifications set out herein illustrate an embodiment of the invention, the embodiment disclosed below is not intended to be exhaustive or to be construed as limiting the scope of the invention to the precise form disclosed.

DETAILED DESCRIPTION

According to FIG. 1, the measurement cell of the densimeter comprises a substantial enclosure having very good heat conductivity which is shown diagrammatically by broken lines and which defines at its inner portion a thermostatic chamber 1.

The thermostatic chamber 1 is closed by a stopper 11 at its upper portion.

The thermostatic chamber 1 contains at its inner portion a U-tube 2 which is kept earthed and which comprises a central limb $2_1$ and also two lateral limbs $2_2$, $2_3$ which extend vertically upwards from the central limb $2_1$.

The two lateral limbs $2_2$, $2_3$ are secured to the stopper 11 at their free ends and project outwardly from the thermostatic chamber 1 in order to permit the injection of a sample being analyzed via an injection opening 4 in the direction of the arrow A and the evacuation of that sample via an evacuation opening 5 in the direction of the arrow B.

The central limb $2_1$ of the U-tube 2 is equipped at its middle portion with a ferromagnetic member 3, the function of which will be explained hereinafter.

The thermostatic chamber 1 also contains at its inner portion an insulated conductive reading plate 6.

The reading plate 6, likewise secured to the stopper 11 in a position facing the U-tube 2, is connected to a high-voltage source 7 so as to be maintained constantly at a difference in potential relative to the tube, and to define a capacitor therewith.

An electromagnetic excitation winding 8 is mounted facing the central limb $2_1$ of the U-tube 2, at right-angles to the ferromagnetic member 3.

The excitation winding 8 is driven by a controller 10 in such a manner that it continuously transmits to the U-tube 2, and more specifically to the ferromagnetic member 3, a synchronised rectangular excitation signal which causes the tube to vibrate at resonance frequency.

The vibration brings about constant variations in the voltage at the terminals of the capacitor 2, 6 which are represented by a sinusoidal resonance signal V=f(t).

That resonance signal, the period of which is a function of the density of the sample being analyzed, is transmitted to an amplifier 9 and is taken off at a control point a in order to enable it to be read on an oscillograph.

The sinusoidal resonance signal is also transmitted continuously to the controller 10 which in return controls the pulse width of the rectangular excitation signal transmitted to the excitation winding 8, in order to maintain the amplitude of the sinusoidal resonance signal at a predefined constant value.

The rectangular excitation signal so regulated, the width of which is a function of the viscosity of the sample being analyzed, is taken off at a control point b in order to enable it to be read on an oscillograph.

Figure 2:
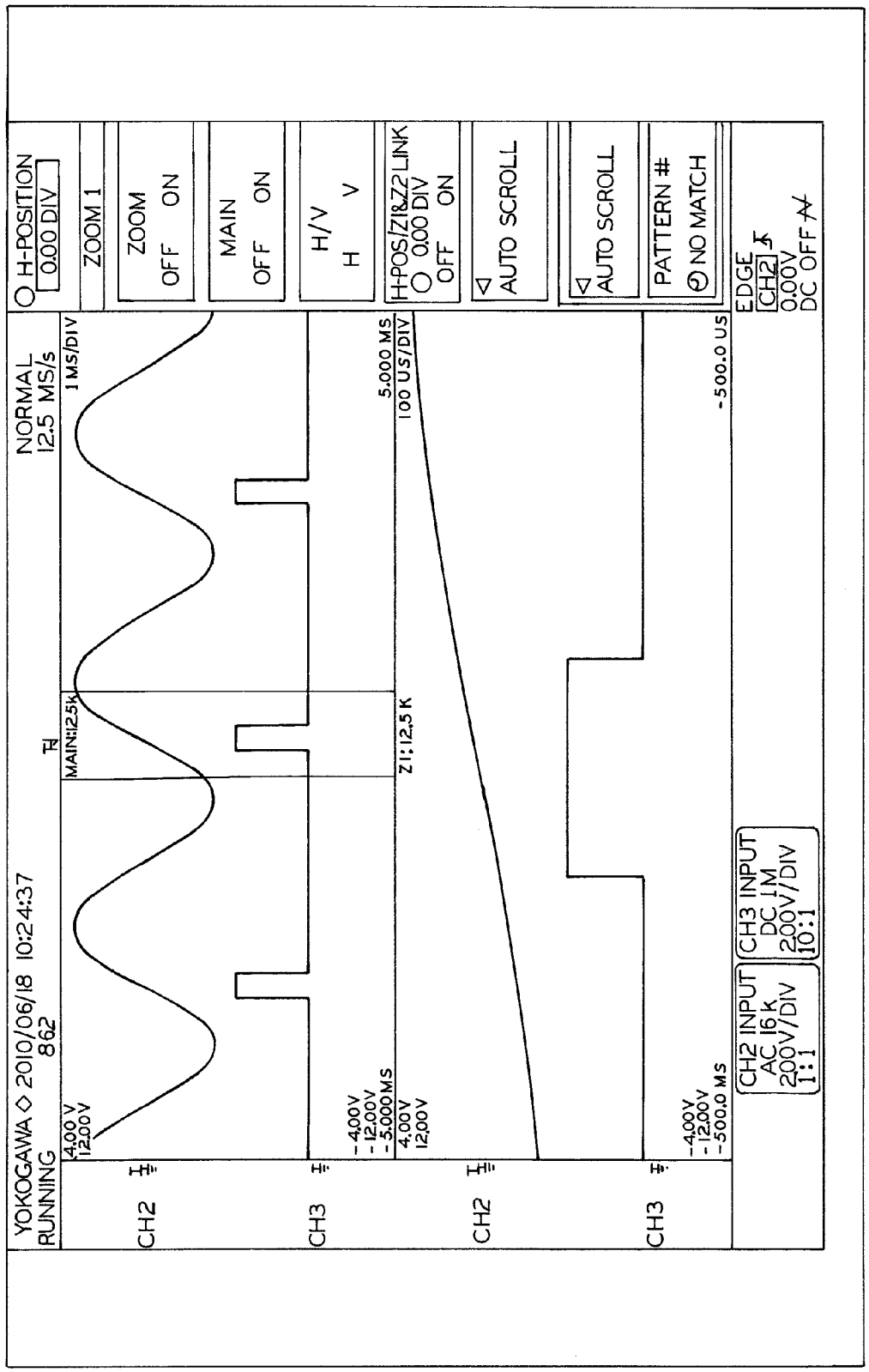
FIGS. 2, 3 and 4 show three examples of oscillograms obtained from such a densimeter when the method according to the invention is used in the case of the analysis of a sample formed by dry air, a weakly viscous sample of density d=0.9 g/ml, and a more strongly viscous sample of density d=0.9 g/ml, respectively.
Figure 3:
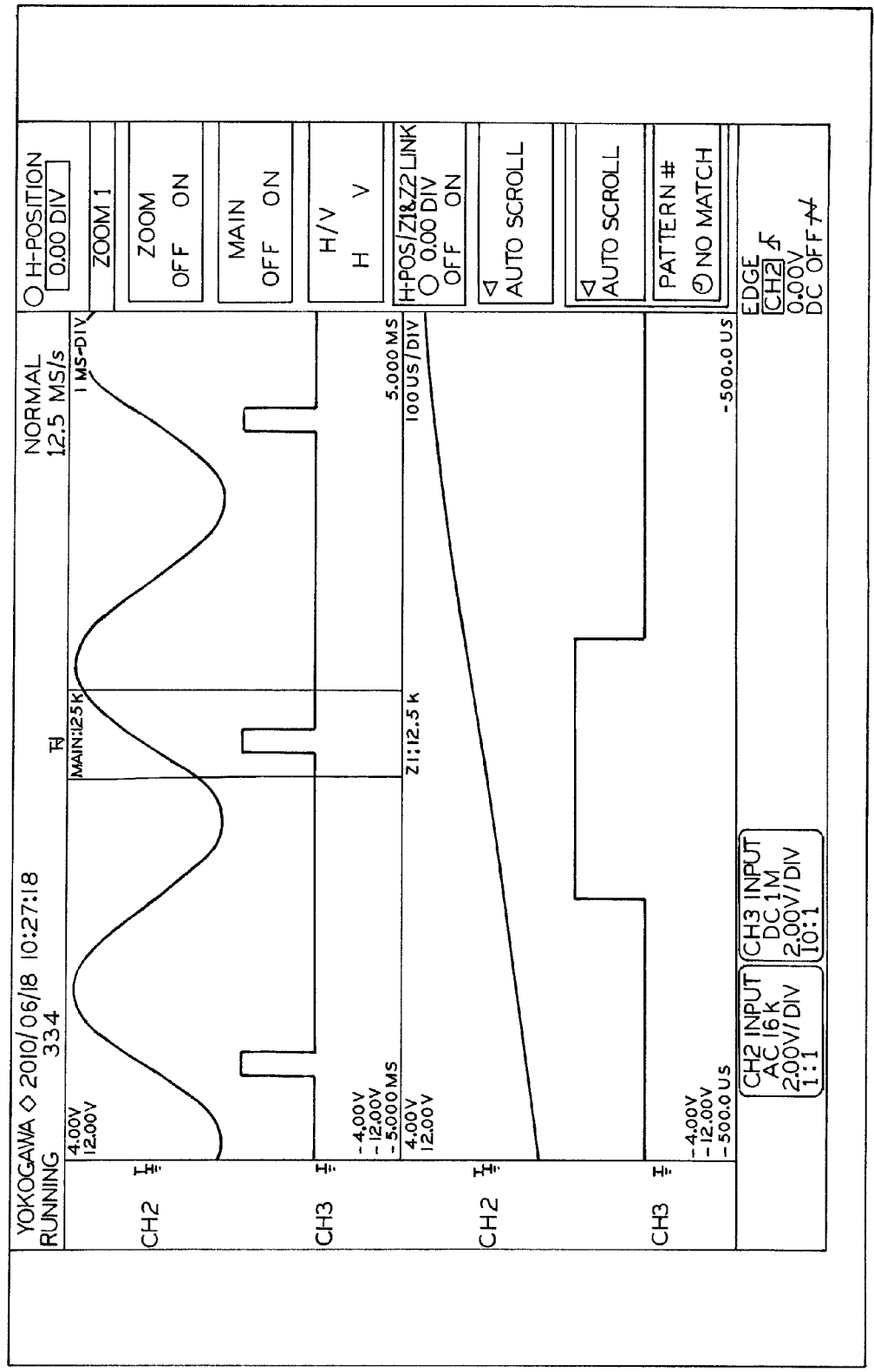
Figure 4:
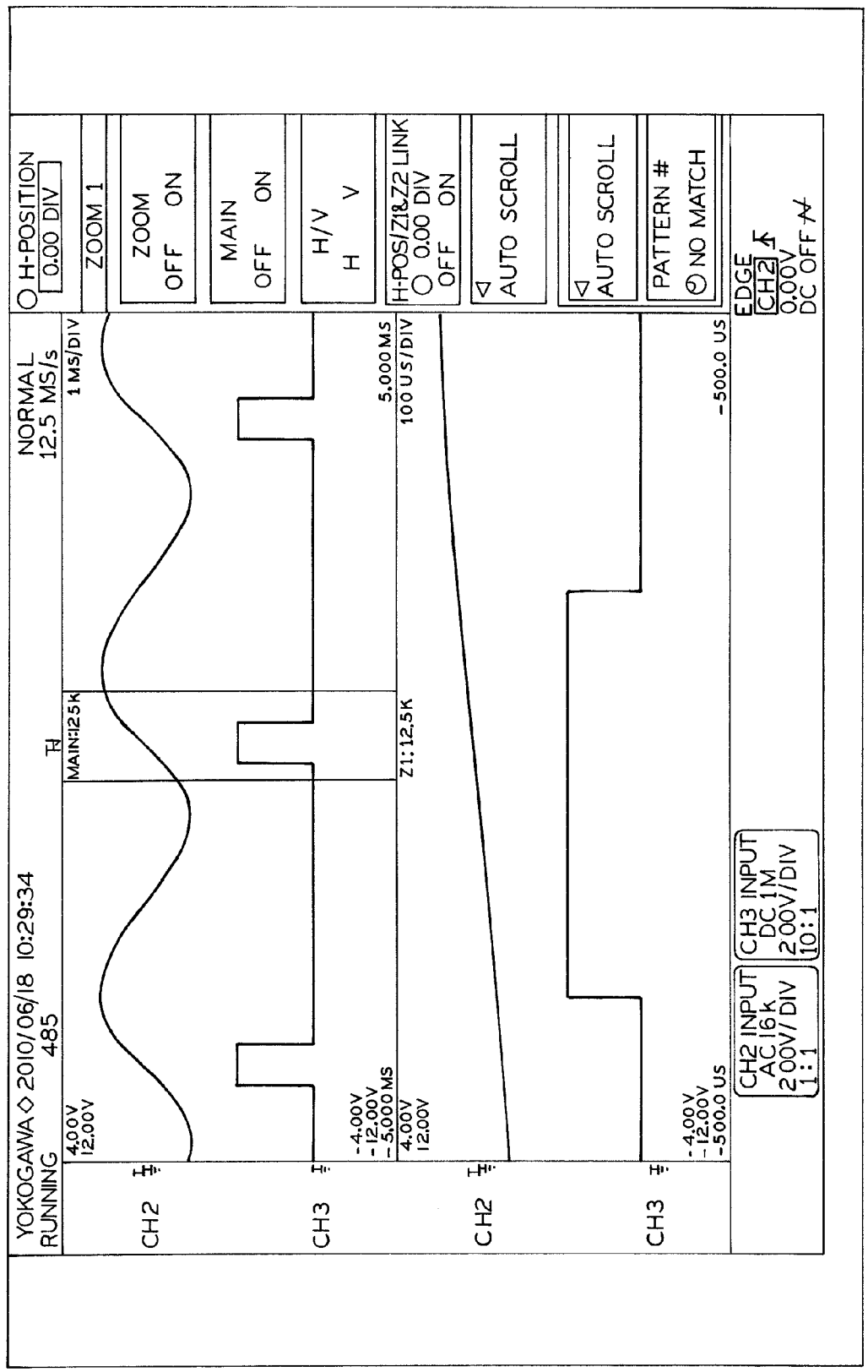

Oscillograms obtained in that manner are shown in FIGS. 2, 3 and 4.

In each of the oscillograms, the sinusoidal resonance signal and the rectangular excitation signal are represented in the upper portion over 2 to 4 vibration periods and in the lower portion with a 10-fold enlargement.

It was thus possible to measure in each case, on the one hand, the period $t_1$ of the sinusoidal resonance signal and, on the other hand, the pulse width $t_2$ of the rectangular excitation signal.

According to FIG. 2, which shows the oscillograms of dry air, that is to say, a sample has not been injected into the U-tube, $t_1 = 2.9\ e^{-3}$ sec and $t_2 = 2.5\ e^{-4}$ sec.

The mass of the U-tube which does not contain a sample is then at a minimum and therefore the resonance frequency is at a maximum and the durations $t_1$ and $t_2$ are also at a minimum.

According to FIG. 3, which shows the oscillograms of a weakly viscous sample of density d=0.9 g/ml, $t_1 = 3.8\ e^{-3}$ sec and $t_2 = 3.1\ e^{-4}$ sec.

Compared with the case shown in FIG. 2, the mass of the tube is greater and therefore the resonance frequency is lower.

In addition, the dissipation of the vibration energy is greater and consequently the controller 10 has to increase the pulse width of the rectangular excitation signal in order to compensate for the decrease in amplitude.

According to FIG. 4, which shows the oscillograms of a more strongly viscous sample of density d=0.9 g/ml, $t_1$=3.8 $e^{-3}$ sec and $t_2$=4.8 $e'^{-4}$ sec.

The resonance frequencies measured on the oscillograms corresponding to FIGS. 3 and 4 are the same in as much as the samples injected into the U-tube have the same density.

On the other hand, according to FIG. 4, taking into account the viscosity of the sample injected, the dissipation of the vibration energy is at a maximum and consequently the pulse width of the rectangular excitation signal is also at a maximum in order to enable the decrease in amplitude to be compensated for.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method for accurately measuring the density of a sample using a densimeter equipped with a measurement cell, the densimeter comprising:
   a heat conductive enclosure including a measurement chamber closed by a stopper;
   a grounded U-tube for containing a sample, the U-tube extending inside the measurement chamber and including a central limb having a ferromagnetic member and two lateral limbs, the lateral limbs secured to the stopper at free ends thereof and projecting outwardly from the measurement chamber to permit the injection of the sample into the U-tube and evacuation of the sample;
   an insulated conductive reading plate maintained at a different potential relative to the U-tube and secured to the stopper in a position facing the U-tube in order to define a capacitor therewith;
   an electromagnetic excitation winding mounted in a housing of the enclosure at a right angle to the ferromagnetic member; and
   means for driving the winding and means for reading the capacity of the capacitor, said method comprising the steps of:
   injecting the sample into the U-tube;
   activating the means for driving the winding to transmit continuously to the U-tube a synchronised rectangular excitation signal to cause the U-tube to vibrate at resonance frequency, the vibration being represented by a sinusoidal resonance signal;
   determining the resonance frequency from the variations in the voltage at the terminals of the capacitor and deducing an approximate value of the density of the sample on the basis of a standard equation;
   controlling the pulse width of the rectangular excitation signal to maintain a predefined constant amplitude of the resonance signal and deducing therefrom a damping effect of the viscosity of the sample on the measurement of density of the sample by measuring the pulse width of the excitation signal, wherein a longer pulse width of the excitation signal correlates to a greater damping effect and a shorter pulse width of the excitation signal correlates to a lesser damping effect; and
   calculating the actual density of the sample on the basis of the approximate value of the density of the sample and the damping effect of viscosity on the measurement of density.

* * * * *